(12) United States Patent
Londeree et al.

(10) Patent No.: US 11,544,552 B1
(45) Date of Patent: Jan. 3, 2023

(54) METHOD AND APPARATUS FOR REFINING AN AUTOMATED CODING MODEL

(71) Applicant: Change Healthcare Holdings, LLC, Nashville, TN (US)

(72) Inventors: Alex Londeree, San Francisco, CA (US); Nick Giannasi, Truckee, CA (US); Adrian Lam, Emeryville, CA (US); Adam Sullivan, Walnut Creek, CA (US)

(73) Assignee: CHANGE HEALTHCARE HOLDINGS, LLC, Nashville, TN (US)

( * ) Notice: Subject to any disclaimer, the term of this patent is extended or adjusted under 35 U.S.C. 154(b) by 707 days.

(21) Appl. No.: 16/369,310

(22) Filed: Mar. 29, 2019

(51) Int. Cl.
  *G06N 3/08* (2006.01)
  *G06N 7/00* (2006.01)

(52) U.S. Cl.
  CPC ............ *G06N 3/08* (2013.01); *G06N 7/005* (2013.01)

(58) Field of Classification Search
  CPC ........... G06N 3/08; G06N 7/005; G16H 15/00
  See application file for complete search history.

(56) References Cited

U.S. PATENT DOCUMENTS

| | | | |
|---|---|---|---|
| 2019/0019582 A1* | 1/2019 | Wallis | G06N 3/04 |
| 2020/0227147 A1* | 7/2020 | Raddatz | G16H 70/60 |

OTHER PUBLICATIONS

Haoran Shi, Pengtao Xie, Zhiting Hu, Ming Zhang, and Eric P. Xing. Towards Automated ICD Coding Using Deep Learning. 2017. Cornell University. (Year: 2017).*
Bum Chul Kwon, Min-Je Choi, Joanne Taery Kim, Edward Choi, Young Bin Kim, Soonwook Kwon, Jimeng Sun, and Jaegul Choo. RetainVis: Visual Analytics with Interpretable and Interactive Recurrent Neural Networks on Electronic Medical Records. Jan. 2019. IEEE. (Year: 2019).*
Wikipedia. Sigmoid Function. 2010. https://en.wikipedia.org/wiki/Sigmoid_function (Year: 2010).*
Towards Automated ICD Coding Using Deep Learning (Shi) taken from https://arxiv.org/pdf/1711.04075.pdf (Year: 2017).*
RetainVis: Visual Analytics with Interpretable and Interactive Recurrent Neural Networks on Electronic Medical Record (Kwon) taken from https://arxiv.org/pdf/1805.10724.pdf (Year: 2018).*
Li, Min, et al. "Automated ICD-9 coding via a deep learning approach." IEEE/ACM transactions on computational biology and bioinformatics 16.4 (2018): 1193-1202. (Year: 2018).*

(Continued)

*Primary Examiner* — Benjamin P Geib
(74) *Attorney, Agent, or Firm* — Myers Bigel, P.A.

(57) ABSTRACT

A method, apparatus and computer program product refine an automated coding model, such as for a medical chart. For each respective candidate code from a set of candidate codes, the method predicts a probability of the respective code being contained in a medical chart. The method also selects one of the candidate codes as being contained in the medical chart based upon the probability and removes the selected candidate code from the set of candidate codes. The method then repeatedly predicts the probability of a respective code being contained in the medical chart, selects one of the candidate codes based upon the predicted probability and removes the selected candidate code from the set of candidate codes. The method further determines a categorical crossentropy loss as to permit adjustment of one or more parameters of the automated coding model.

18 Claims, 3 Drawing Sheets

(56) References Cited

OTHER PUBLICATIONS

Baumel, Tal, et al. "Multi-label classification of patient notes: case study on ICD code assignment." Workshops at the thirty-second AAAI conference on artificial intelligence. 2018. (Year: 2018).*

Xu, Keyang, et al. "Multimodal Machine Learning for Automated ICD Coding." arXiv preprint arXiv:1810.13348 (2018). (Year: 2018).*

P. Nguyen, T. Tran, N. Wickramasinghe and S. Venkatesh, "Deepr : A Convolutional Net for Medical Records," in IEEE Journal of Biomedical and Health Informatics, vol. 21, No. 1, pp. 22-30, Jan. 2017, doi: 10.1109/JBHI.2016.2633963 (Year: 2017).*

Chahbandarian, Ghazar, et al. "Increasing secondary diagnosis encoding quality using data mining techniques." 2016 IEEE Tenth International Conference on Research Challenges in Information Science (RCIS). IEEE, 2016. (Year: 2016).*

\* cited by examiner

METHOD AND APPARATUS FOR REFINING AN AUTOMATED CODING MODEL

TECHNOLOGICAL FIELD

An example embodiment relates generally to secondary diagnosis prediction using deep learning based machine learning and, more particularly, to the refinement of an automated coding model, such as for a medical chart.

BACKGROUND

Deep learning models can be utilized to generate various predictions across a dataset, with the predictions then utilized for a wide variety of purposes. Predictive modeling including that provided by deep learning models is a critical part of automation and, as such, the use of predictive modeling is correspondingly increasing.

By way of example of use of a predictive model, medical charts are analyzed in order to identify a primary diagnosis and zero or more secondary diagnoses contained within the medical chart. The identification of the diagnoses is utilized for various purposes, such as in conjunction with healthcare transactions including, for example, requests for payment or reimbursement by an insurer or other third party.

While the use of a predictive model to predict the diagnoses contained in a medical chart increases the efficiency with which the medical charts may be coded, the large number of candidate secondary diagnoses, such as tens of thousands of candidate secondary diagnoses, can make it difficult to use existing techniques to extract the particular secondary diagnoses that should be applied to the chart. As such, predictive models may sometimes be less accurate than is desired, potentially leading to reduced confidence in the resulting predictions and corresponding reduction in the rate of adoption or utilization of the predictive models.

Deep learning models are traditionally trained via gradient descent optimization utilizing backpropagation. This process uses a neural network to generate a prediction, and then evaluates that prediction using a cost or loss function to generate an error signal. This error signal is then propagated through the network to produce an update direction and scale for each parameter in the network so that the next time that the network is executed, the network generates a prediction that produces a lower value for the loss function. However, designing an appropriate loss function is not only critical in training a deep learning model, but can be challenging, thereby leading to some of the inaccuracy with respect to the use of predictive models.

BRIEF SUMMARY

A method, apparatus and computer program product are provided in accordance with an example embodiment in order to refine an automated coding model for a medical chart. In this regard, the method, apparatus and computer program product of an example embodiment determine a categorical crossentropy loss based on probabilities that are predicted for candidate codes in order to permit adjustment of one or more parameters of the automated coding model based upon the categorical crossentropy loss. By refining the automated coding model, the resulting code prediction may be more accurate, thereby providing for increased confidence in the automated coding model and potentially increased rates of adoption and/or utilization.

In an example embodiment, a method is provided for refining an automated coding model for secondary diagnosis prediction. For each respective candidate secondary diagnosis from a set of candidate secondary diagnoses, the method predicts a probability of the respective secondary diagnosis being contained in a medical chart. The method also selects one of the candidate secondary diagnoses as being contained in the medical chart based upon the probability that is predicted and removes the candidate secondary diagnosis that has been selected from the set of candidate secondary diagnoses. Following removal of the candidate secondary diagnosis that has been selected from the set of secondary diagnoses, the method repeatedly predicts the probability of a respective secondary diagnosis being contained in the medical chart, selects one of the candidate secondary diagnoses as being contained in the medical chart based upon the probability that is predicted and removes the candidate secondary diagnosis that has been selected from the set of candidate secondary diagnoses. The method further determines a categorical crossentropy loss based upon the probabilities that are predicted for the candidate secondary diagnoses that are selected so as to permit adjustment of one or more parameters of the automated coding model based upon the categorical crossentropy loss.

The method of an example embodiment selects one of the candidate secondary diagnoses by selecting the candidate secondary diagnosis having the greatest probability of being contained in the medical chart. In an example embodiment, the method predicts the probability of a respective secondary diagnosis being contained in a medical chart by predicting the probability such that a cumulative probability of the plurality of candidate secondary diagnoses from the set of candidate secondary diagnoses equals 1. The method of an example embodiment determines the categorical crossentropy loss by determining, for each of the candidate secondary diagnoses that are selected, a product of a label representative of a respective candidate secondary diagnosis that is selected and the probability of the respective candidate secondary diagnosis. The categorical crossentropy loss of this example embodiment is then determined by summing the products for each of the candidate secondary diagnoses that are selected to determine the categorical crossentropy loss.

The method of an example embodiment also includes adjusting the one or more parameters of the automated coding model based upon the categorical crossentropy loss to reduce the categorical crossentropy loss. In an example embodiment, the method removes the candidate secondary diagnosis that has been selected from the set of candidate secondary diagnoses by removing the candidate secondary diagnosis that has been selected and one or more additional candidate secondary diagnoses that have a defined relationship to the candidate secondary diagnosis that has been selected from the set of candidate secondary diagnoses. In an example embodiment in which the set of candidate secondary diagnoses also includes a null element, the repeated predicting, selection and removal is concluded upon selecting the null element based upon the probability of the null element that is predicted.

In another example embodiment, an apparatus is provided for refining an automated coding model for secondary diagnosis prediction. The apparatus includes prediction circuitry configured to predict, for each respective candidate secondary diagnosis from a set of candidate secondary diagnoses, a probability of the respective secondary diagnosis being contained in a medical chart. The prediction circuitry is also configured to select one of the candidate secondary diagnoses as being contained in the medical chart based upon the probability that is predicted and to remove the candidate secondary diagnosis that has been selected from the set of candidate secondary diagnoses. Following removal of the candidate secondary diagnosis that has been selected from the set of secondary diagnoses, the prediction circuitry is configured to repeatedly predict the probability of a respective secondary diagnosis being contained in the medical chart, select one of the candidate secondary diagnoses as being contained in the medical chart based upon the probability that is predicted and remove the candidate secondary diagnosis that has been selected from the set of candidate secondary diagnoses. The apparatus also includes loss determination circuitry configured to determine a categorical crossentropy loss based upon the probabilities that are predicted for the candidate secondary diagnoses that are selected so as to permit adjustment of one or more parameters of the automated coding model based upon the categorical crossentropy loss.

The prediction circuitry of an example embodiment is configured to select one of the candidate secondary diagnoses by selecting the candidate secondary diagnosis having the greatest probability of being contained in the medical chart. In an example embodiment, the prediction circuitry is configured to predict the probability of a respective secondary diagnosis being contained in a medical chart by predicting the probability such that a cumulative probability of the plurality of candidate secondary diagnoses from the set of candidate secondary diagnoses equals 1. The loss determination circuitry of an example embodiment is configured to determine the categorical crossentropy loss by determining, for each of the candidate secondary diagnoses that are selected, a product of a label representative of a respective candidate secondary diagnosis that is selected and the probability of the respective candidate secondary diagnosis. The loss determination circuitry of this example embodiment is also configured to determine the categorical crossentropy loss by summing the products for each of the candidate secondary diagnoses that are selected to determine the categorical crossentropy loss.

The apparatus of an example embodiment also includes model adjustment circuitry configured to adjust the one or more parameters of the automated coding model based upon the categorical crossentropy loss to reduce the categorical crossentropy loss. In an example embodiment, the prediction circuitry is configured to remove the candidate secondary diagnosis that has been selected from the set of candidate secondary diagnoses by removing the candidate secondary diagnosis that has been selected and one or more additional candidate secondary diagnoses that have a defined relationship to the candidate secondary diagnosis that has been selected from the set of candidate secondary diagnoses. In an embodiment in which the set of candidate secondary diagnoses also includes a null element, the prediction circuitry is configured such that repeatedly predicting, selecting and removing concludes upon selecting the null element based upon the probability of the null element that is predicted.

In a further example embodiment, a computer program product is provided that includes at least one non-transitory computer-readable storage medium for refining an automated coding model for secondary diagnosis prediction. The at least one non-transitory computer-readable storage medium store software instructions that, when executed, cause an apparatus to predict, for each respective candidate secondary diagnosis from a set of candidate secondary diagnoses, a probability of the respective secondary diagnosis being contained in a medical chart. The software instructions also cause the apparatus to select one of the candidate secondary diagnoses as being contained in the medical chart based upon the probability that is predicted and to remove the candidate secondary diagnosis that has been selected from the set of candidate secondary diagnoses. Following removal of the candidate secondary diagnosis that has been selected from the set of secondary diagnoses, the software instructions further cause the apparatus to repeatedly predict the probability of a respective secondary diagnosis being contained in the medical chart, select one of the candidate secondary diagnoses as being contained in the medical chart based upon the probability that is predicted and remove the candidate secondary diagnosis that has been selected from the set of candidate secondary diagnoses. The software instructions additionally cause the apparatus to determine a categorical crossentropy loss based upon the probabilities that are predicted for the candidate secondary diagnoses that are selected so as to permit adjustment of one or more parameters of the automated coding model based upon the categorical crossentropy loss.

In an example embodiment, the software instructions to select one of the candidate secondary diagnoses include software instructions to select the candidate secondary diagnosis having the greatest probability of being contained in the medical chart. In accordance with an example embodiment, the software instructions to predict the probability of a respective secondary diagnosis being contained in a medical chart include software instructions to predict the probability such that a cumulative probability of the plurality of candidate secondary diagnoses from the set of candidate secondary diagnoses equals 1. The software instructions to determine the categorical crossentropy loss include, in an example embodiment, software instructions to determine, for each of the candidate secondary diagnoses that are selected, a product of a label representative of a respective candidate secondary diagnosis that is selected and the probability of the respective candidate secondary diagnosis and software instructions to sum the products for each of the candidate secondary diagnoses that are selected to determine the categorical crossentropy loss.

The software instructions of an example embodiment further include software instructions to adjust the one or more parameters of the automated coding model based upon the categorical crossentropy loss to reduce the categorical crossentropy loss. In an example embodiment, the software instructions to remove the candidate secondary diagnosis that has been selected from the set of candidate secondary diagnoses include software instructions to remove the candidate secondary diagnosis that has been selected and one or more additional candidate secondary diagnoses that have a defined relationship to the candidate secondary diagnosis that has been selected from the set of candidate secondary diagnoses.

In yet another example embodiment, a method, apparatus and computer program product are provided for refining an automated coding model for a medical chart. For each respective candidate code, such as a secondary diagnosis code, a procedure code and/or a revenue code, from a set of candidate codes, a probability is predicted of the respective candidate code being contained in a medical chart. One of the candidate codes is selected as being contained in the medical chart based upon the probability that is predicted and removes the candidate code that has been selected from the set of candidate codes. Following removal of the candidate code that has been selected from the set of candidate codes, the method, apparatus and computer program product repeatedly predict the probability of a respective candidate code being contained in the medical chart, selects one of the candidate codes as being contained in the medical chart based upon the probability that is predicted and removes the candidate code that has been selected from the set of candidate codes. A categorical crossentropy loss is then determined based upon the probabilities that are predicted for the candidate codes that are selected so as to permit adjustment of one or more parameters of the automated coding model based upon the categorical crossentropy loss.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Having described certain example embodiments of the present disclosure in general terms above, reference will now be made to the accompanying drawings, which are not necessarily drawn to scale and wherein.

DETAILED DESCRIPTION

Figure 1:
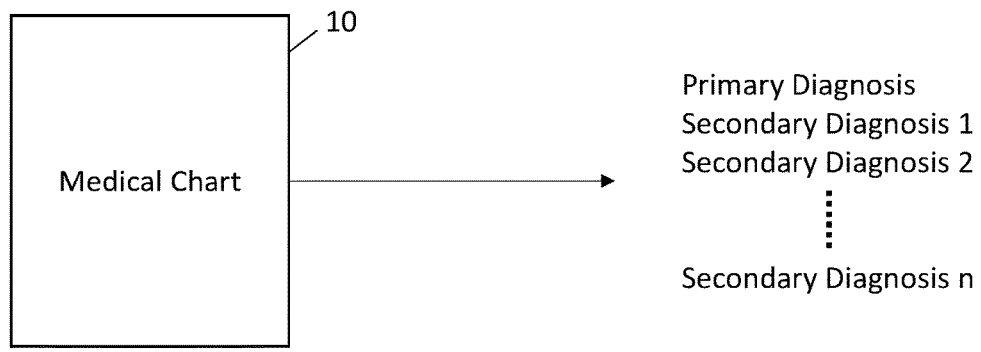
FIG. 1 is a representation of the primary diagnosis and a plurality of secondary diagnoses contained in a medical chart.

Some embodiments of the present disclosure will now be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout. As used herein, the terms "data," "content," "information," and similar terms may be used interchangeably to refer to data capable of being transmitted, received, and/or stored in accordance with embodiments of the present invention. Thus, use of any such terms should not be taken to limit the spirit and scope of embodiments of the present invention.

Models are frequently utilized in order to make predictions from a data set. For example, systems that incorporate artificial intelligence may utilize various predictive models including deep learning models. A model is oftentimes defined by a plurality of different parameters and the model may be trained, such as based upon data sets for which the predicted value(s) are known, by modifying or tuning the parameters of the model such that the model provides predictions with increased accuracy. For example, a deep learning model may be trained by a gradient descent optimization process utilizing back propagation. In this regard, the deep learning model generates a predication that is then evaluated by a cost or loss function to determine an error associated with the prediction. The error is then propagated through the model to modify the model parameters. In this regard, the propagation of the error through the model may produce an update direction and scale for each parameter such that subsequent execution of the model results in a smaller error. To permit the model to be efficiently trained, such as in terms of the processing time and resources required for the training, the design and implementation of the loss function is significant.

One example of a predictive model relates to an automated coding model for predicting codes, such as diagnosis codes, procedure codes and/or revenue codes, from a medical chart. The medical chart may be a medical record, e.g., an electronic medical record (EMR), and may include information regarding the patient as well as detailed information regarding various encounters that the patient has had with one or more healthcare practitioners, such as office visits, tests that have been conducted or the like.

In addition to being informative for the healthcare practitioners, the medical chart may be utilized for a wide variety of other purposes. For example, one or more healthcare transactions may be generated based on the medical chart. These healthcare transactions may include, for example, healthcare transactions by which a provider requests payment or reimbursement from an insurance company or other third party payer. Other healthcare transactions include, for example, the determination of a patient co-pay amount, the coordination of benefits or the like. These and other healthcare transactions are generated based upon a patient encounter as memorialized by the patient's medical chart and are at least partially dependent upon the codes, such as the diagnosis codes, the procedure codes and/or the revenue codes, contained in a medical chart. As such, the reliable prediction of the codes, including the diagnosis codes, the procedure codes and/or the revenue codes, contained in a medical chart is of import in relation to the generation of healthcare transactions that accurately reflect the patient encounter represented by the medical chart.

However, medical charts oftentimes include substantial quantities of information that may be a challenge to properly code in terms of the diagnosis codes, procedure codes and/or revenue codes, contained in the medical chart. As such, automated coding models have been developed in order to predict the codes, e.g., associated with the diagnoses including the secondary diagnoses, contained in a medical chart. However, there are a large number of potential codes, e.g., diagnoses, contained in a medical chart with tens of thousands of candidate codes, e.g., secondary diagnoses, to be considered. As such, the application of at least some automated coding models, such as an automated coding model that relies upon the determination of a binary crossentropy loss, may be unable to consistently identify the codes, e.g., the secondary diagnosis codes, procedure codes and/or revenue codes, contained in a medical chart.

A method, apparatus and computer program product are therefore provided in accordance with an example embodiment in order to refine an automated coding model for a medical chart. Utilizing the automated coding model, a medical chart 10 as shown in FIG. 1 may be reviewed and various codes that are representative of the content of the medical chart are predicted, such as by predicting the primary diagnosis as well as a plurality of secondary diagnoses that are contained in the medical chart. Any number of codes, such as secondary diagnosis codes, procedure codes and/or revenue codes, may be predicted from a medical chart, but, in one embodiment, a maximum number of candidate secondary diagnoses is predefined, such as a maximum of 25 secondary diagnoses.

An apparatus for refining an automated coding model for a medical chart may be embodied by any of a variety of computing devices. Example embodiments may include a plurality of networked devices operating in a distributed system. In this regard, it will be understood that the term "distributed system" refers to a plurality of networked devices in which some components are shared among the devices. Whether or not the apparatus is implemented using a distributed system, the apparatus of an example embodiment may be embodied by any of a variety of fixed terminals, such as servers, desktop computers, mainframe devices, kiosks, or the like. Such example computing devices may additionally or alternatively comprise any of a variety of mobile terminals, such as portable digital assistants (PDAs), mobile telephones, smartphones, laptop computers, tablet computers, or any combinations of the aforementioned devices.

Figure 2:
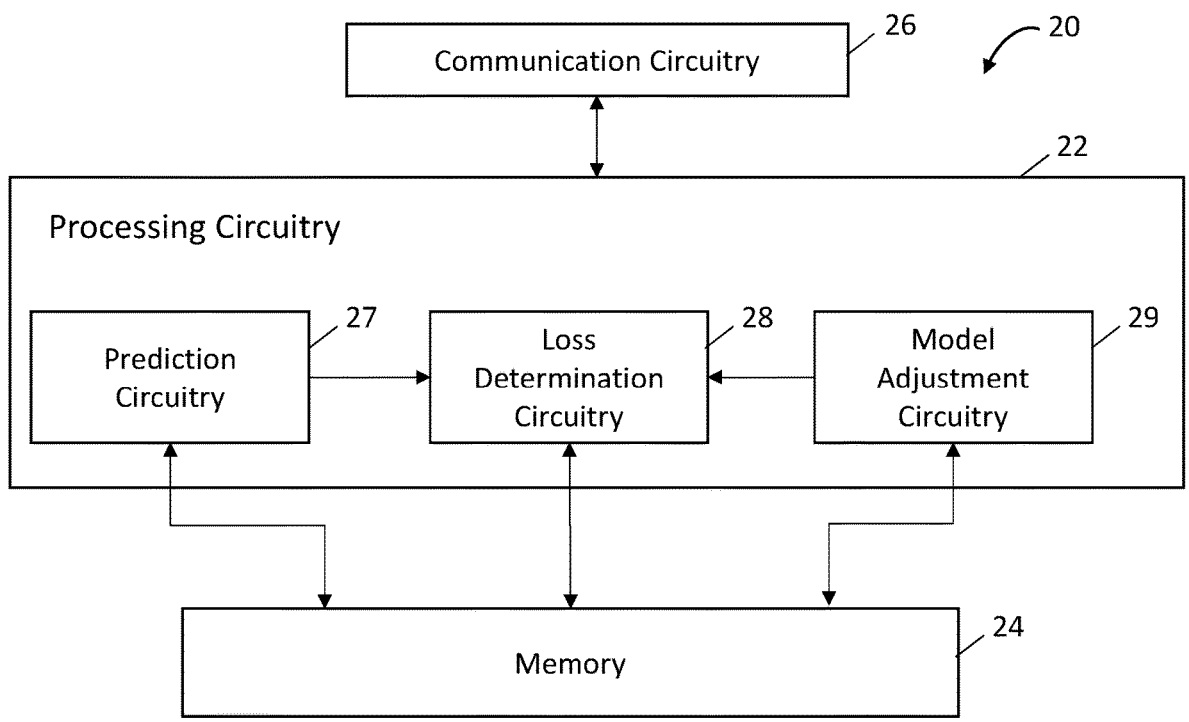
FIG. 2 is a block diagram of an apparatus specifically configured in accordance with an example embodiment of the present disclosure.

Turning to FIG. 2, an example apparatus 20 is illustrated that may be configured to perform the operations described herein, thereby implementing a predictive model, such as a deep learning model, that, in turn, employs a neural network. The apparatus includes processing circuitry 22, a memory 24, and optionally communications circuitry 26. The apparatus also includes prediction circuitry 27, loss determination circuitry 28 and model adjustment circuitry 29. As described below, the prediction circuitry, loss determination circuitry and model adjustment circuitry may be embodied by the processing circuitry. Alternatively, the prediction circuitry, loss determination circuitry and model adjustment circuitry may be separate and distinct from the processing circuitry. In an embodiment in which the prediction circuitry, loss determination circuitry and model adjustment circuitry are distinct from the processing circuitry, the prediction circuitry, loss determination circuitry and model adjustment circuitry may be embodied in the same manner as described below with respect to the processing circuitry. The apparatus may be configured to execute the operations described below in connection with FIGS. 3 and 4.

In some embodiments, the processing circuitry 22 and, in some embodiments, the prediction circuitry 27, loss determination circuitry 28 and model adjustment circuitry 29, may be in communication with the memory 24 via a bus for passing information among components of the apparatus. The processing circuitry and, in some embodiments, the prediction circuitry, loss determination circuitry and model adjustment circuitry, may be embodied in a number of different ways and may, for example, include one or more processing devices configured to perform independently. Additionally or alternatively, the processing circuitry and, in some embodiments, the prediction circuitry, loss determination circuitry and model adjustment circuitry, may include one or more processors configured in tandem via a bus to enable independent execution of software instructions, pipelining, and/or multithreading. The use of the terms "processor" or "processing circuitry" may be understood to include a single core processor, a multi-core processor, multiple processors of the apparatus 20, remote or "cloud" processors, or any combination thereof In an example embodiment, the processing circuitry 22 and, in some embodiments, the prediction circuitry 27, loss determination circuitry 28 and model adjustment circuitry 29, may be configured to execute software instructions stored in the memory 24 or otherwise accessible to the processing circuitry. Alternatively or additionally, the processing circuitry and, in some embodiments, the prediction circuitry, loss determination circuitry and model adjustment circuitry, may be configured to execute hard-coded functionality. As such, whether configured by hardware or software methods, or by a combination of hardware with software, the processing circuitry and, in some embodiments, the prediction circuitry, loss determination circuitry and model adjustment circuitry, may represent an entity (e.g., physically embodied in circuitry) capable of performing operations according to an embodiment of the present invention while configured accordingly. Alternatively, as another example, when the processing circuitry and, in some embodiments, the prediction circuitry, loss determination circuitry and model adjustment circuitry, are embodied as an executor of software instructions, the software instructions may specifically configure the circuitry to perform the algorithms and/or operations described herein when the software instructions are executed.

Memory 24 is non-transitory and may include, for example, one or more volatile and/or non-volatile memories. In other words, for example, the memory may be an electronic storage device (e.g., a computer readable storage medium). The memory may be configured to store information, data, content, applications, software instructions, or the like, for enabling the apparatus 20 to carry out various functions in accordance with example embodiments contemplated herein.

The communications circuitry 26 may be any means such as a device or circuitry embodied in either hardware or a combination of hardware and software that is configured to receive and/or transmit data from/to a network and/or any other device, circuitry, or module in communication with the apparatus 20. In this regard, the communications circuitry may include, for example, a network interface for enabling communications with a wired or wireless communication network. For example, the communications circuitry may include one or more network interface cards, antennas, buses, switches, routers, modems, and supporting hardware and/or software, or any other device suitable for enabling communications via a network. Additionally or alternatively, the communication interface may include the circuitry for causing transmission of such signals to a network or to handle receipt of signals received from a network.

Although the processing circuitry 22, the prediction circuitry 27, the loss determination circuitry 28 and the model adjustment circuitry 29 may, in part, be described using functional language, it will be understood that the particular implementations necessarily include the use of particular hardware. It should also be understood that certain of these components may include similar or common hardware. For example, the prediction circuitry, the loss determination circuitry and the model adjustment circuitry may each at times leverage use of the processing 22 or memory, but duplicate hardware is not required to facilitate operation of these distinct components of the apparatus 20 (although duplicated hardware components may be used in some embodiments, such as those in which enhanced parallelism may be desired). The use of the term "circuitry" as used herein with respect to components of the apparatus therefore shall be interpreted as including the particular hardware configured to perform the functions associated with the particular circuitry described herein. Of course, while the term "circuitry" should be understood broadly to include hardware, in some embodiments, the term "circuitry" may refer also to software instructions that configure the hardware components of the apparatus to perform their various functions.

To this end, each of the processing circuitry 22, the prediction circuitry 27, the loss determination circuitry 28 and the model adjustment circuitry 29 may include one or more dedicate processor, specially configured field programmable gate array (FPGA), or application specific interface circuit (ASIC) to perform its corresponding functions, these components may additionally or alternatively be implemented using a processor executing software stored in a memory (e.g., memory 24). In this fashion, the processing circuitry and, in some embodiments, the prediction circuitry, the loss determination circuitry and the model adjustment circuitry are therefore implemented using special-purpose components implemented purely via hardware design or may utilize hardware components of the apparatus 20 that execute computer software designed to facilitate performance of the functions of the processing circuitry, audit assignment circuitry, record modification, filtration circuitry, and machine learning model.

As will be appreciated based on this disclosure, example embodiments contemplated herein may be implemented by apparatus 20. Furthermore, embodiments may take the form of a computer program product on at least one non-transitory computer-readable storage medium (e.g., memory 24) storing software instructions. Any suitable non-transitory computer-readable storage medium may be utilized, some examples of which are non-transitory hard disks, CD-ROMs, flash memory, optical storage devices, and magnetic storage devices. It should be appreciated, with respect to certain devices embodied by apparatus as described in FIGS. 3 and 5, that loading the software instructions onto a computer or apparatus produces a special-purpose machine comprising the means for implementing various functions described herein.

Figure 3:
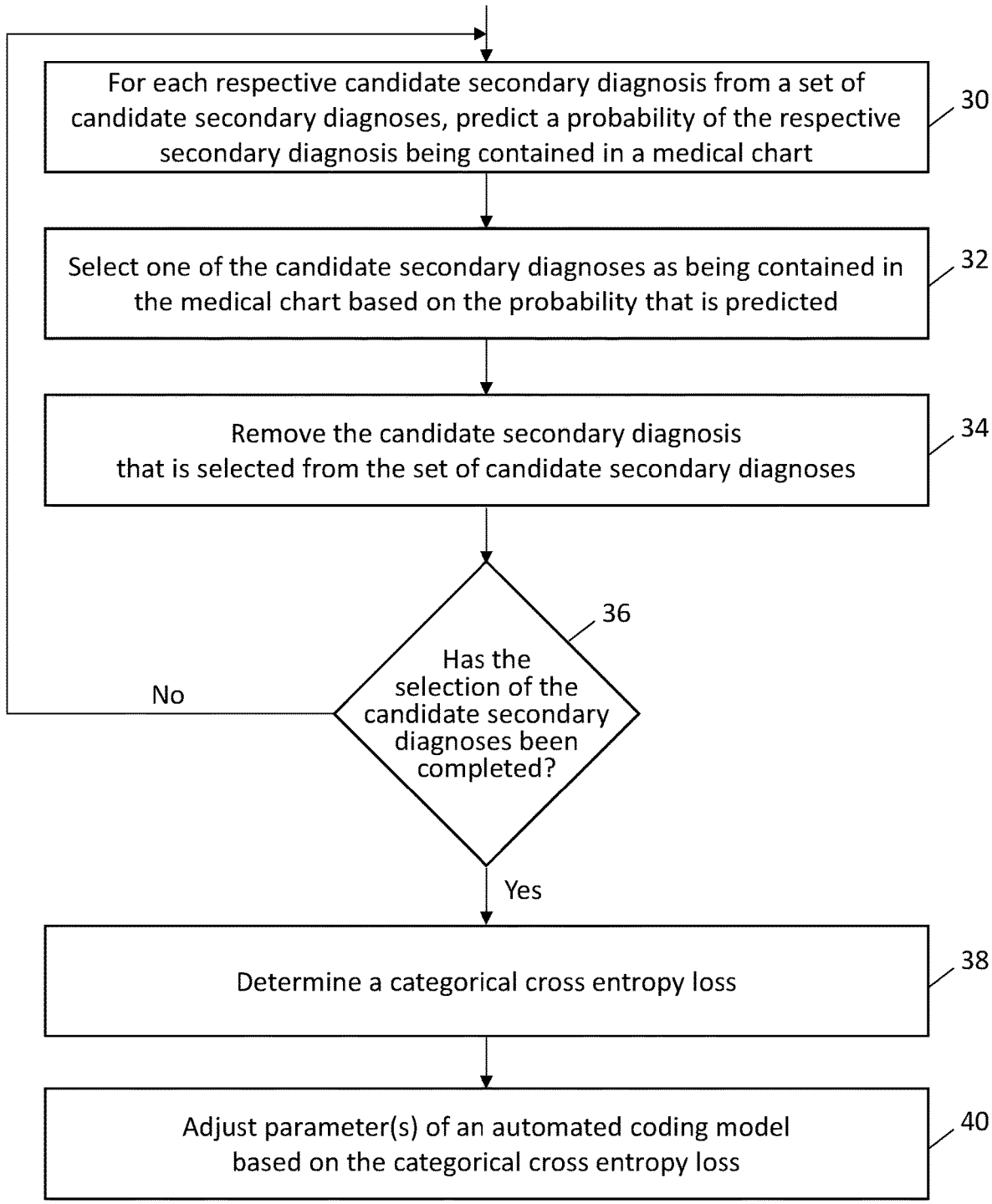
FIG. 3 is a flow chart illustrating operations performed, such as by the apparatus of FIG. 2, in order to refine an automated coding model for secondary diagnosis prediction in accordance with an example embodiment of the present disclosure.

Referring now to FIG. 3, the operations performed, such as by the apparatus 20 of FIG. 2, in order to refine an automated coding model for predicting the codes representative of a medical chart are illustrated. Although described hereinafter in conjunction with the prediction of candidate secondary diagnoses from a medical chart, the method and apparatus of an example embodiment may additionally or alternatively be configured to predict other types of codes from the medical record including, for example, procedure codes and/or revenue codes. With reference to the example embodiment, however, the candidate secondary diagnoses are initially predicted, such as in an iterative process as described below and as may be implemented by a recurrent layer of a neural network, such as a long short-term memory (LSTM) layer. In this regard and as shown in block 30, for each candidate secondary diagnosis from a set of candidate secondary diagnoses, the apparatus includes means, such as the processing circuitry 22, the prediction circuitry 27 or the like, configured to predict the probability of respective secondary diagnoses being contained in the medical chart 10. In an example embodiment, the set of secondary diagnoses that is considered during this first iteration is the entire set of predefined secondary diagnoses. The set of secondary diagnoses may be stored by the memory 24 or may be otherwise accessible by the processing circuitry, such as the prediction circuitry.

The set of candidate secondary diagnoses may additionally include, in one embodiment, not only the candidate secondary diagnoses, but also a null element. The null element is included in the label space and the probability of the null element is predicted in the same manner that the probabilities of the candidate secondary diagnoses are predicted. In this regard, the probability of the null element is representative of the probability that none of the candidate secondary diagnoses from the set of candidate secondary diagnoses is contained in the medical chart 10.

For each candidate secondary diagnosis within the set of candidate secondary diagnoses, the processing circuitry 22, such as the prediction circuitry 27, is configured to determine the predicted probability of the respective secondary diagnosis being contained within the medical chart. This prediction may be based upon the coding model that is utilized for secondary diagnosis prediction. This coding model may be predefined, such as based upon prior training of the coding model. The coding model may also be stored by the memory 24 or may otherwise be otherwise accessible by the processing circuitry, such as the prediction circuitry. As a result of the probability prediction for each candidate secondary diagnosis, every candidate secondary diagnosis from the set of candidate secondary diagnoses has an associated probability. In an example embodiment, the sum of the probabilities for the set of candidate secondary diagnoses equals 1.

As shown in block 32 of FIG. 3, the apparatus 20 also includes means, such as the processing circuitry 22, the prediction circuitry 27 or the like, configured to select one of the candidate secondary diagnoses as being contained in the medical chart. This selection is based upon the probabilities that are predicted for the candidate secondary diagnoses. In an example embodiment, the processing circuitry, such as the prediction circuitry, is configured to select the candidate secondary diagnosis having the greatest probability of being contained in the medical chart, that is, the softmax output from an analysis of the probabilities that are predicted for the candidate secondary diagnoses.

In an example embodiment, the apparatus 20, such as the processing circuitry 22, the prediction circuitry 27 or the like, is configured to assign a label to the candidate secondary diagnosis that has been selected. Although the label may be configured in various manners, the label of an example embodiment is an array, such as a linear array, with each element representative of a different iteration of the process for predicting candidate secondary diagnoses that are contained in the medical chart 10. Thus, the label of a candidate secondary diagnosis that has been selected may be a linear array in which the elements are all zeros, other than the element associated with the particular iteration during which the respective candidate secondary diagnosis that has been selected which is set to 1. Thus, in an example embodiment in which up to 25 candidate secondary diagnoses are predicted in an iterative fashion, the labels identifying the different candidate secondary diagnoses that are selected during the different iterations would have 25 elements, each associated with a respective iteration and each being set to 0 other than the element associated with the iteration during which the candidate secondary diagnosis was selected, which is set to 1. For the candidate secondary diagnosis that is selected during the first iteration as described above, the label that is assigned may be a linear array of 25 elements (since the predefined maximum number of candidate secondary diagnoses of this example embodiment is 25) with the first element associated with the first iteration being set to 1 as a result of the selection of the candidate secondary diagnosis during the first iteration and with the other elements being set to 0. By way of example, labels can be represented as a single n-hot array, e.g., a one-hot array, with each value of the array corresponding to an element in the target set (the set of candidate secondary diagnoses) being given a 1 value and every other given a 0 value.

Once selected, the processing circuitry 22, such as the prediction circuitry 27, is configured to store the candidate secondary diagnosis that has been selected and the probability that has been predicted for the selected candidate secondary diagnosis. The label associated with the selected candidate secondary diagnosis may also be stored in association therewith.

As shown in block 34 of FIG. 3, the apparatus 20 of this example embodiment also includes means, such as the processing circuitry 22, the prediction circuitry 27 or the like, configured to remove the candidate secondary diagnosis that has been selected from the set of candidate secondary diagnoses. In some embodiments, only the candidate secondary diagnosis that has been selected is removed from the set of candidate secondary diagnoses. In other embodiments, however, one or more additional candidate secondary diagnoses may be associated with, e.g., jointly attached to, the candidate secondary diagnosis that is selected. In these example embodiments, selection of the candidate secondary diagnosis and the removal of the selected candidate secondary diagnosis also causes the additional candidate secondary diagnoses that are associated with the candidate secondary diagnosis that has been selected to also be removed from the set of candidate secondary diagnoses.

The association between the candidate secondary diagnoses may be predefined and stored, for example, in memory 24 in a manner that is accessible to the processing circuitry 22, such as the prediction circuitry 27. The association may be defined in various manners, but, in some embodiments, the association between candidate secondary diagnoses is based upon the similarity between the candidate secondary diagnoses. In these embodiments, the selection of one of the candidate secondary diagnoses that have been predefined to have an association effectively represents the other associated candidate secondary diagnoses as well. Alternatively, the association between the candidate secondary diagnoses may be based upon the alternative nature of the candidate secondary diagnoses that are associated. In this example embodiment, the selection of a candidate secondary diagnosis from among the candidate secondary diagnoses that are associated may also cause the other associated candidate secondary diagnoses that are alternatives to and mutually exclusive of the candidate secondary diagnosis that has been selected to also be removed from the set of candidate secondary diagnoses since the associated candidate secondary diagnoses are no longer viable options to be contained in the medical chart 10 as a result of the selection of a candidate secondary diagnosis that has a mutually exclusive relationship to the other candidate secondary diagnoses that are associated therewith. For example, the set of candidate secondary diagnoses may include A101, A102, A103, B202 and C303. The candidate secondary diagnoses A101, A102 and A103 may be mutually exclusive options such that upon selection of A101, A102 and A103 are removed from the set of candidate secondary diagnoses along with the removal of A101. Thus, the result set of candidate secondary diagnoses now includes B202 and C303. By removing these other candidate secondary diagnoses from the set of candidate secondary diagnoses based upon their association with the candidate secondary diagnosis that has been selected, the method, apparatus 20 and computer program product of an example embodiment may refine the automated coding model with greater computational efficiency since the resulting set of candidate secondary diagnoses to consider is smaller.

As shown in decision block 36, the apparatus 20 includes means, such as the processing circuitry 22, the prediction circuitry 27 or the like, configured to determine whether the selection of the candidate secondary diagnosis from the set of candidate secondary diagnoses has been completed and, if not, to perform another iteration of the functions depicted by blocks 30, 32 and 34. Each prediction either produces a potential label or a null prediction. As a result, the maximum set size is the number of generated predictions, not the size of the label space. The predicted set is the set of labels that are predicted as candidate secondary diagnosis having the greatest probability during each iteration unless that label corresponds to the null prediction.

With respect to the completion of the iterative prediction process, the processing circuitry 22, such as the prediction circuitry 27, is configured to determine if the predefined maximum number of candidate secondary diagnoses has been selected. In an instance in which the maximum number of candidate secondary diagnoses has been selected, the processing circuitry, such as the predication circuitry, of an example embodiment, is configured to determine that the iterative process of selecting the candidate secondary diagnoses from the set of candidate secondary diagnoses has been completed.

In other embodiments, however, the iterative process may be determined to have been completed prior to selecting the predefined maximum number of candidate secondary diagnoses. For example, in an embodiment in which the set of candidate secondary diagnoses includes not only the candidate secondary diagnoses, but also a null element, the apparatus 20, such as the processing circuitry 22, the prediction circuitry 27 or the like, is configured to determine that the selection of the candidate secondary diagnoses has been completed in an instance in which the candidate secondary diagnosis that is selected during the most recent iteration is the null element indicating, for example, that the greatest probability from among the candidate secondary diagnoses remaining in the set of candidate secondary diagnoses is that none of the candidate secondary diagnoses in the set are contained in the medical chart 10.

In an instance in which the selection of the candidate secondary diagnoses is determined to not have been completed, the apparatus 20 includes means, such as the processing circuitry 22, the prediction circuitry 27 or the like, configured to perform another iteration of the process for predicting candidate secondary diagnoses that are contained in the medical chart 10. In this regard, the processing circuitry, such as the prediction circuitry, is configured to repeat the prediction of the probability of a respective secondary diagnosis being contained in the medical chart as shown in block 30, the selection of one of the candidate secondary diagnoses as being contained in the medical chart based upon the probability that is predicted as shown in block 32 and the removal of the candidate secondary diagnosis that has been selected from the set of candidate secondary diagnoses as shown in block 34. Thus, the iterative process is repeated until the processing circuitry, such as the prediction circuitry, determines that the selection of the candidate secondary diagnoses have been completed as shown in block 36.

During each iteration, the set of candidate secondary diagnoses that is analyzed is different than the set of candidate secondary diagnoses that was previously analyzed during a prior iteration as a result of the removal of the candidate secondary diagnosis that was selected during the prior iteration from the set. Thus, the probabilities that are predicted for the remaining members of the set of candidate secondary diagnoses may vary from one iteration to the next as a result of the application of the coding model.

With each iteration of the process, a different candidate secondary diagnosis is selected. Thus, with reference to the example of FIG. 1, the first iteration may result in the selection of Secondary Diagnosis 1, the second iteration may result in the selection of Secondary Diagnosis 2 and so on until the selection of the candidate secondary diagnoses has been completed. In FIG. 1, the iterative process has continued until the predefined maximum number, e.g., 25, of candidate secondary diagnoses has been selected with the final selection being Secondary Diagnosis 25. Notwithstanding the numerical designation of the candidate secondary diagnoses based upon the iteration during which a secondary diagnosis was selected, the candidate secondary diagnoses may be an unordered subset of the set of candidate secondary diagnoses.

Once the selection of the candidate secondary diagnoses has been completed, the apparatus 20 includes means, such as the processing circuitry 22, the loss determination circuitry 28 or the like, configured to determine a categorical crossentropy loss based upon the probabilities that are predicted for the candidate secondary diagnoses that were selected. Based upon the a categorical crossentropy loss, the parameters of the predictive model, such as the deep learning model, implemented by the apparatus may be modified, thereby training the model to permit more accurate prediction of the secondary diagnoses during subsequent utilization of the predictive model. The categorical crossentropy loss may be determined in various manners. In an example embodiment depicted in block 50 of FIG. 4, for example, the apparatus includes means, such as the processing circuitry, the loss determination circuitry or the like, configured to identify a respective candidate secondary diagnosis from among the candidate secondary diagnoses that have been selected. The processing circuitry, such as the loss determination circuitry, may be configured to identify a respective candidate secondary diagnosis in various manners. In an example embodiment, however, the processing circuitry, such as the loss prediction circuitry, is configured to sequentially identify the candidate secondary diagnoses in the order in which the candidate secondary diagnoses were iteratively selected. As such, the processing circuitry, such as the loss prediction circuitry, of an example embodiment initially identifies the candidate secondary diagnosis that was selected during the first iteration, e.g., Secondary Diagnosis 1.

Figure 4:
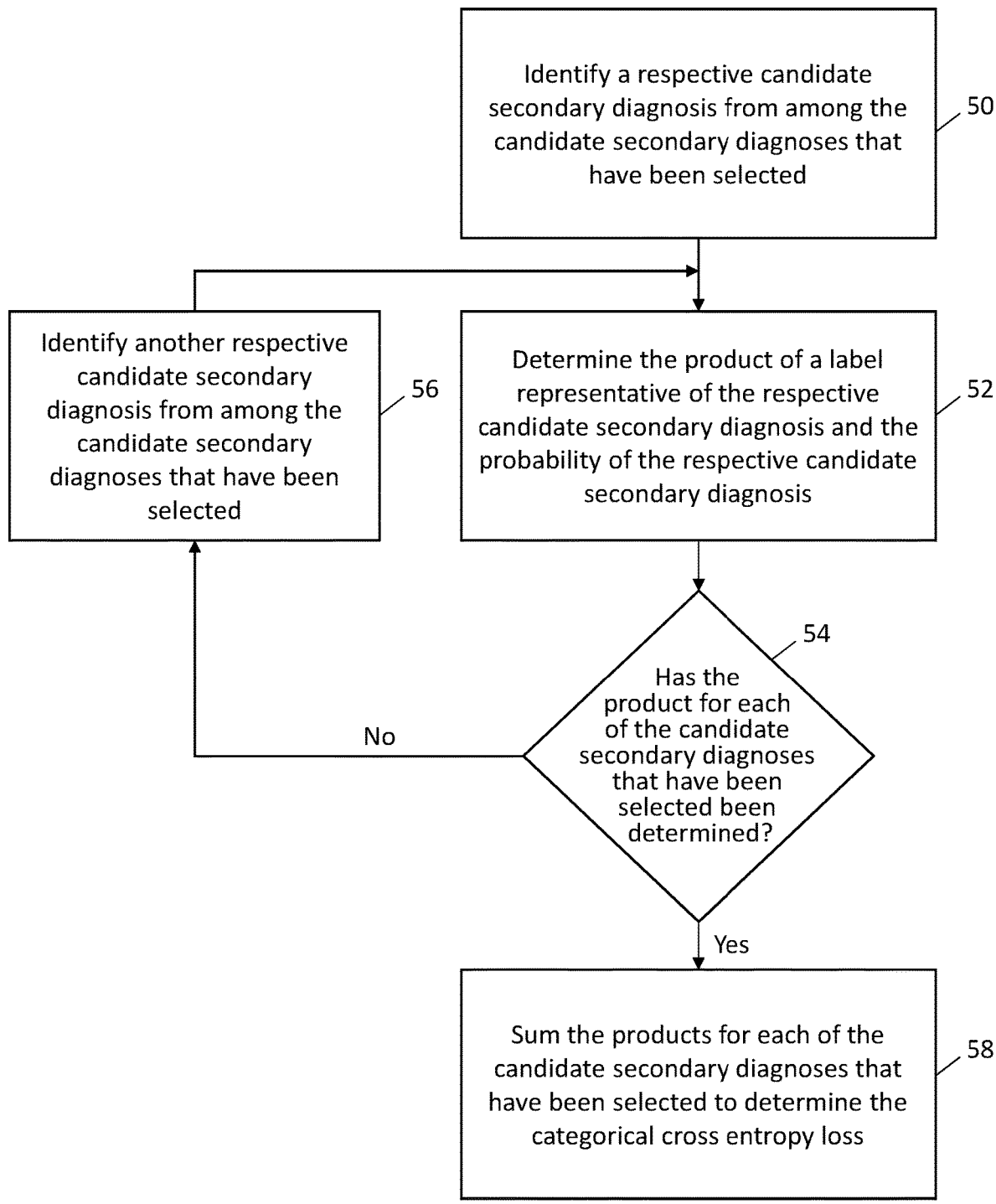
FIG. 4 is a flow chart illustrating operations performed, such as by the apparatus of FIG. 2, in order to determine the categorical crossentropy loss in accordance with an example embodiment of the present disclosure.

As shown in block 52 of FIG. 4 and following identification of a respective candidate secondary diagnosis, the apparatus 20 of this example embodiment also includes means, such as the processing circuitry 22, the loss determination circuitry 28 or the like, configured to determine the product of the label representative of the respective candidate secondary diagnosis that was identified and the probability associated with the respective candidate secondary diagnosis. In this regard, the probability of the respective candidate secondary diagnosis is the probability that was predicted for the respective candidate secondary diagnosis and was relied upon during the selection of the candidate secondary diagnosis.

As shown in decision block 54, the apparatus 20 of this example embodiment also includes means, such as the processing circuitry 22, the loss determination circuitry 28 or the like, configured to determine whether the product for each of the candidate secondary diagnoses that have been selected has been determined. In other words, the processing circuitry, such as the loss determination circuitry, is configured to determine whether the product of the candidate secondary diagnosis selected during each iteration described above has been determined. In an instance in which the product for each of the candidate secondary diagnoses that have been selected has not yet been determined, the apparatus includes means, such as the processing circuitry, the loss determination circuitry or the like, configured to identify another respective candidate secondary diagnosis from among the candidate secondary diagnoses that have been selected but for which a product has not yet been determined. See block 56. In the foregoing example, the processing circuitry, such as the loss determination circuitry, may be configured to identify the respective candidate secondary diagnosis that was selected during the next iteration (that is, the next iteration relative to the iteration that resulted in the selection of the respective candidate secondary diagnosis for which a product was most recently determined.) Thus, following determination of the product associated with the candidate secondary diagnosis selected during the first iteration, e.g., Secondary Diagnosis 1, the candidate secondary diagnosis selected during the second iteration, e.g., Secondary Diagnosis 2, is identified, and so on. This process is repeated until each of the candidate secondary diagnoses that have been selected have been identified and the corresponding product has been determined.

Following determination of the product for each of the candidate secondary diagnoses that have been selected and as shown in block 58 of FIG. 4, the apparatus 20 also includes means, such as the processing circuitry 22, the loss determination circuitry 28 or the like, configured to sum the products for each of the candidate secondary diagnoses that have been selected to determine the categorical crossentropy loss. In an example embodiment, the apparatus, such as the processing circuitry, the loss determination circuitry or the like, is configured to determine the combined categorical crossentropy loss as followis:

$$loss = \sum_{i=0}^{n} -\log(y'_i \cdot f_i(x \mid \theta))$$

wherein $f_i(x|\theta)$ is the $i^{th}$ prediction of the neural network of the predictive model given input x (that is, the set of candidate secondary diagnoses) and parameters θ (the modifiable parameters of the neural network). Each prediction represents a class probability distribution over all possible secondary diagnoses and adding up with the null prediction to a probability of 1. $y'_i$ is a one-hot encoding (a vector of zeros for each class except the label class that is designated with a 1) of the selected label for the $i^{th}$ prediction and n is the number of candidate secondary diagnoses that were selected, such as the maximum number of candidate secondary diagnoses. With respect to the selection of the labels, $y_i$ and $y'_i$ can be defined as follows:

$$y'_i = onehot(\mathrm{argmax}(y_i * f_i(x|\theta)))$$

$$y_{i+1} = \begin{cases} y_i - y'_i, & \sum y_i > 1 \\ y^o, & \sum y_i \le 1 \end{cases}$$

wherein $y_i$ is the label group aggregated up until that point, $y_0$ is an n-hot encoding of all possible true values for that (x, y) pair (in this case a 0 for every possible label except the secondary diagnoses already applied to the document). $y^o$ is a one-hot vector representing the null prediction (meaning the set has been exhausted).

In the example embodiment in which labels are represented as a single n-hot array with each value of the array corresponding to an element in the target set (the set of candidate secondary diagnoses) being given a 1 value and every other value of the array given a 0 value, the apparatus 20, such as the processing circuitry 22, the loss determination circuitry 28 or the like, is configured to determine the loss as described above by iteratively removing 1 values from this vector as the 1 values are selected for use in the loss function until the vector contains only zeros. Then, in an example embodiment, the selection process from the resulting vector would be to select the null prediction. In other embodiments, a null prediction may not be made, such as in an instance in which the predicted set is as large or larger than the maximum set size.

The categorical crossentropy loss is a measure of the loss attributable to the coding model. For example, a smaller categorical crossentropy loss may be representative of a coding model having a greater confidence value and a greater accuracy in relation to the prediction of secondary diagnoses from a medical chart. By way of another example, a larger categorical crossentropy loss may be representative of a coding model having a reduced confidence value and lower accuracy in relation to the prediction of secondary diagnoses from a medical chart.

As shown in block 40 of FIG. 3, the apparatus 20 of an example embodiment also includes means, such as the processing circuitry 22, the model adjustment circuitry 29 or the like, configured to adjust one or more parameters of the automated coding model based upon the categorical crossentropy loss in order to reduce the categorical crossentropy loss for subsequent predictions of secondary diagnoses from a medical chart. In this regard, after modifying one or more parameters of the coding model based upon the categorical crossentropy loss, the foregoing process described above in relation to FIG. 3 may then be repeated utilizing the coding model having the one or more parameters that have been modified. The resulting categorical crossentropy loss associated with the secondary diagnoses predicted by the modified coding model may then be compared to the categorical crossentropy loss from the prior prediction of the secondary diagnoses contained by the medical chart. The processing circuitry, such as the model adjustment circuitry, may continue to modify the parameters of the coding model and to then repeat the process of predicting secondary diagnoses contained in the medical chart and determining the resulting categorical crossentropy loss until the categorical crossentropy loss is minimized, is reduced to at least a satisfactory level or is the lowest from among the categorical crossentropy losses determined following application of the coding model with different sets of parameters, at which point the parameters of the coding model are fixed.

By way of illustration, but not of limitation, one example of the method, apparatus and computer program product determines a categorical crossentropy loss based on probabilities that are predicted for candidate secondary diagnoses in an instance in which there are 5 possible diagnoses and a maximum set size of 3. Although there are 5 possible diagnoses, namely, [A419, J189, N179, B20, G935], the medical chart of this example actually only includes the second and fourth diagnoses such that the y label for diagnoses [A419, J189, N179, B20, G935] is as follows:

$$y_0 = [0, 1, 0, 1, 0, 0]$$

After execution of the automated coding model, the output of the automated coding model may be as follows:

$$f_0(x|\theta) = [0.01, 0.02, 0.005, 0.95, 0.005, 0.01]$$

$$f_1(x|\theta) = [0.01, 0.95, 0.005, 0.02, 0.005, 0.01]$$

$$f_2(x|\theta) = [0.01, 0.02, 0.005, 0.01, 0.005, 0.95]$$

For the first iteration:
prediction$_0$=argmax($f_0(x|\theta)$)=3 which is the index for the most probable secondary diagnosis, that is, B20
y'$_0$=onehot(argmax($y_0 * f_0(x|\theta)$))=onehot(argmax([0, 1, 0, 1, 0, 0]*[0.01, 0.02, 0.005, 0.95, 0.005, 0.01]))=onehot(argmax([0, 0.02, 0, 0.95, 0, 0]))=onehot(3)=[0, 0, 0, 1, 0, 0]

$$\Sigma y_0 = \Sigma [0, 1, 0, 1, 0, 0] = 2 \text{ so}$$

$$y_1 = y_0 - y'_0 = [0, 1, 0, 1, 0, 0] - [0, 0, 0, 1, 0, 0] = [0, 1, 0, 0, 0, 0]$$

The loss for the first iteration may then be determined as:

$$loss_0 = -\log(y'_0 \cdot f_0(x|\theta)) = -\log([0, 0, 0, 1, 0, 0] \cdot [0.01, 0.02, 0.005, 0.95, 0.005, 0.01]) = -\log(0.95) = 0.05129$$

For the second iteration:
prediction$_1$=argmax($f_1(x|\theta)$)=1 which is the index for the most probable secondary diagnosis, that is, J189
y'$_1$=onehot(argmax($y_1 * f_1(x|\theta)$))=onehot(argmax([0, 1, 0, 0, 0, 0]*[0.01, 0.95, 0.005, 0.02, 0.005, 0.01]))=onehot(argmax([0, 0.95, 0, 0, 0, 0]))=onehot(1)=[0, 1, 0, 0, 0, 0]

$$\Sigma y_1 = \Sigma [0, 1, 0, 0, 0, 0] = 1 \text{ so}$$

$$y_2 = y^o = [0, 0, 0, 0, 0, 1]$$

The loss for the second iteration may then be determined as:

$$loss_1 = -\log(y'_1 \cdot f_1(x|\theta)) = -\log([0, 1, 0, 0, 0, 0] \cdot [0.01, 0.95, 0.005, 0.02, 0.005, 0.01]) = -\log(0.95) = 0.05129$$

And for the third iteration:

$$prediction_2 = argmax(f_2(x|\theta)) = 5$$

As the five elements of the set of possible diagnoses have indices of 0, 1, 2, 3 and 4, the prediction of an index of 5 represents the null element and is an indication that there are no additional diagnoses in the set that are candidates to be predicted. The third iteration of this example continues as follows:

y'$_2$=onehot(argmax($y_2 * f_2(x|\theta)$))=onehot(argmax([0, 0, 0, 0, 0, 1]*[0.01, 0.02, 0.005, 0.01, 0.005, 0.95]))=onehot(argmax([0, 0, 0, 0, 0, 0.95]))=onehot(5)=[0, 0, 0, 0, 0, 1]

The loss for the third iteration may then be determined as:

$$loss_2 = -\log(y'_2 \cdot f_2(x|\theta)) = -\log([0, 0, 0, 0, 0, 1] \cdot [0.01, 0.02, 0.005, 0.01, 0.005, 0.95]) = -\log(0.95) = 0.05129$$

Based on the losses from each iteration, the final loss would be:

$$loss = \Sigma -\log(y'_i \cdot f_i(x|\theta)) = \Sigma losses = \Sigma [0.05129, 0.05129, 0.05129] = 0.15388$$

And the final prediction would be:

$$prediction = \{B20, J189\}$$

In the foregoing example, the automated coding model predicts the two secondary diagnoses, that is, B20 and J189, contained in the medical chart. In addition, the value of the final loss may be utilized to update the parameters of the automated coding model, both in terms of magnitude and direction, in order to improve subsequent predictions. Although the parameters of the automated coding model may be updated in various manners, automatic differentiation may be applied, based upon the final loss value, to update the parameters of the automated coding model. In this regard, automatic differentiation numerically evaluate the functions performed by a computer program, such as the computer program executed by the processor 22, in order to update the parameters of the automated coding model.

As such, the coding model may be refined to permit a more accurate prediction of the secondary diagnosis contained in a medical chart. In this regard, the coding model is refined so as to be at least partially defined by the one or more parameters that permit the secondary diagnoses contained in the medical chart to be predicted in a manner that has a categorical crossentropy loss that has been determined to be satisfactory, such as by being the lowest categorical crossentropy loss. As such, the confidence in and the accuracy of the automated prediction of the secondary diagnoses contained in the medical chart may be increased by modifying the coding model in accordance with the categorical crossentropy loss.

As described above, the coding model may predict not only the secondary diagnosis contained in a medical chart, but other codes, such as procedure codes and/or revenue codes, contained in a medical chart, either in addition to or instead of the prediction of the secondary diagnosis. Still further, the method and apparatus of an example embodiment may be configured to make predictions of one or more elements of a larger set in other contexts and for other applications in addition to or instead of the analysis of a medical chart including, for example, in conjunction with audits, such as audits of a financial institution, indemnification and/or real estate.

FIGS. 3 and 4 illustrate flowcharts describing the operation of apparatuses, methods, and computer program products according to example embodiments of the invention. It will be understood that each block of the flowcharts, and combinations of blocks in the flowcharts, may be implemented by various means, embodied as hardware, firmware, circuitry, and/or other devices associated with execution of software including one or more software instructions. For example, one or more of the operations described above may be embodied by software instructions. In this regard, the software instructions which embody the procedures described above may be stored by a memory of an apparatus 20 employing an embodiment of the present invention and executed by processing circuitry 22 and, in some embodiments, the prediction circuitry 27, the loss determination circuitry 28 and the model adjustment circuitry 29 of the apparatus. As will be appreciated, any such software instructions may be loaded onto a computer or other programmable apparatus (e.g., hardware) to produce a machine, such that the resulting computer or other programmable apparatus implements the functions specified in the flowchart blocks. These software instructions may also be stored in a computer-readable memory that may direct a computer or other programmable apparatus to function in a particular manner, such that the software instructions stored in the computer-readable memory produce an article of manufacture, the execution of which implements the functions specified in the flowchart blocks. The software instructions may also be loaded onto a computer or other programmable apparatus to cause a series of operations to be performed on the computer or other programmable apparatus to produce a computer-implemented process such that the software instructions executed on the computer or other programmable apparatus provide operations for implementing the functions specified in the flowchart blocks.

The flowchart blocks support combinations of means for performing the specified functions and combinations of operations for performing the specified functions. It will be understood that one or more blocks of the flowcharts, and combinations of blocks in the flowcharts, can be implemented by special purpose hardware-based computer systems which perform the specified functions, or combinations of special purpose hardware and software instructions.

In some embodiments, some of the operations above may be modified or further amplified. Furthermore, in some embodiments, additional optional operations may be included. Modifications, amplifications, or additions to the operations above may be performed in any order and in any combination.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method for refining an automated coding model for secondary diagnosis prediction, the method comprising:
   operating a deep learning model including an artificial neural network to perform operations as follows:
   for each respective candidate secondary diagnosis from a set of candidate secondary diagnoses, predicting a probability of the respective secondary diagnosis being contained in a medical chart;
   selecting one of the candidate secondary diagnoses as being contained in the medical chart based upon the probability that is predicted and removing the candidate secondary diagnosis that has been selected from the set of candidate secondary diagnoses;
   following removal of the candidate secondary diagnosis that has been selected from the set of secondary diagnoses, repeatedly predicting the probability of a respective secondary diagnosis being contained in the medical chart, selecting one of the candidate secondary diagnoses as being contained in the medical chart based upon the probability that is predicted and removing the candidate secondary diagnosis that has been selected from the set of candidate secondary diagnoses; and
   determining a categorical crossentropy loss based upon the probabilities that are predicted for the candidate secondary diagnoses that are selected;
   adjusting one or more parameters of the artificial neural network, which implements the automated coding model, based upon the categorical crossentropy loss, wherein the set of candidate secondary diagnoses also includes a null element, and wherein repeatedly predicting, selecting and removing is concluded upon selecting the null element based upon the probability of the null element that is predicted.

2. A method according to claim 1 wherein selecting one of the candidate secondary diagnoses comprises selecting the candidate secondary diagnosis having the greatest probability of being contained in the medical chart.

3. A method according to claim 1 wherein predicting the probability of a respective secondary diagnosis being contained in a medical chart comprises predicting the probability such that a cumulative probability of the plurality of candidate secondary diagnoses from the set of candidate secondary diagnoses equals 1.

4. A method according to claim 1 wherein determining the categorical crossentropy loss comprises:
for each of the candidate secondary diagnoses that are selected, determining a product of a label representative of a respective candidate secondary diagnosis that is selected and the probability of the respective candidate secondary diagnosis; and
summing the products for each of the candidate secondary diagnoses that are selected to determine the categorical crossentropy loss.

5. A method according to claim 1 further comprising adjusting the one or more parameters of the automated coding model based upon the categorical crossentropy loss to reduce the categorical crossentropy loss.

6. A method according to claim 1 wherein removing the candidate secondary diagnosis that has been selected from the set of candidate secondary diagnoses comprises removing the candidate secondary diagnosis that has been selected and one or more additional candidate secondary diagnoses that have a defined relationship to the candidate secondary diagnosis that has been selected from the set of candidate secondary diagnoses.

7. An apparatus for refining an automated coding model for secondary diagnosis prediction, the apparatus comprising:
a processor; and
a memory coupled to the processor and comprising computer readable program code embodied in the memory that is executable by the processor to operate a deep learning model including an artificial neural network to perform operations comprising:
predicting, for each respective candidate secondary diagnosis from a set of candidate secondary diagnoses, a probability of the respective secondary diagnosis being contained in a medical chart;
selecting one of the candidate secondary diagnoses as being contained in the medical chart based upon the probability that is predicted and remove the candidate secondary diagnosis that has been selected from the set of candidate secondary diagnoses; and
following removal of the candidate secondary diagnosis that has been selected from the set of secondary diagnoses, repeatedly predicting the probability of a respective secondary diagnosis being contained in the medical chart, select one of the candidate secondary diagnoses as being contained in the medical chart based upon the probability that is predicted and remove the candidate secondary diagnosis that has been selected from the set of candidate secondary diagnoses; and determining a categorical crossentropy loss based upon the probabilities that are predicted for the candidate secondary diagnoses that are selected;
adjusting one or more parameters of the artificial neural network, which implements the automated coding model, based upon the categorical crossentropy loss,
wherein the set of candidate secondary diagnoses includes a null element, and wherein repeatedly predicting, selecting and removing is concluded upon selecting the null element based upon the probability of the null element that is predicted.

8. An apparatus according to claim 7 wherein selecting one of the candidate secondary diagnoses comprises selecting the candidate secondary diagnosis having the greatest probability of being contained in the medical chart.

9. An apparatus according to claim 7 wherein predicting the probability of a respective secondary diagnosis being contained in a medical chart comprises predicting the probability such that a cumulative probability of the plurality of candidate secondary diagnoses from the set of candidate secondary diagnoses equals 1.

10. An apparatus according to claim 7 wherein determining the categorical crossentropy loss comprises:
for each of the candidate secondary diagnoses that are selected, determining a product of a label representative of a respective candidate secondary diagnosis that is selected and the probability of the respective candidate secondary diagnosis; and
summing the products for each of the candidate secondary diagnoses that are selected to determine the categorical crossentropy loss.

11. An apparatus according to claim 7 wherein the operations further comprise:
adjusting the one or more parameters of the automated coding model based upon the categorical crossentropy loss to reduce the categorical crossentropy loss.

12. An apparatus according to claim 7 wherein removing the candidate secondary diagnosis that has been selected from the set of candidate secondary diagnoses comprises removing the candidate secondary diagnosis that has been selected and one or more additional candidate secondary diagnoses that have a defined relationship to the candidate secondary diagnosis that has been selected from the set of candidate secondary diagnoses.

13. A computer program product, comprising:
a non-transitory computer readable storage medium comprising computer readable program code embodied in the medium that is executable by a processor to perform operations comprising:
operating a deep learning model including an artificial neural network to perform operations as follows:
for each respective candidate secondary diagnosis from a set of candidate secondary diagnoses, predicting a probability of the respective secondary diagnosis being contained in a medical chart;
selecting one of the candidate secondary diagnoses as being contained in the medical chart based upon the probability that is predicted and removing the candidate secondary diagnosis that has been selected from the set of candidate secondary diagnoses;
following removal of the candidate secondary diagnosis that has been selected from the set of secondary diagnoses, repeatedly predicting the probability of a respective secondary diagnosis being contained in the medical chart, selecting one of the candidate secondary diagnoses as being contained in the medical chart based upon the probability that is predicted and removing the candidate secondary diagnosis that has been selected from the set of candidate secondary diagnoses; and determining a categorical crossentropy loss based upon the probabilities that are predicted for the candidate secondary diagnoses that are selected;

adjusting one or more parameters of the artificial neural network, which implements the automated coding model, based upon the categorical crossentropy loss, wherein the set of candidate secondary diagnoses also includes a null element, and wherein repeatedly predicting, selecting and removing is concluded upon selecting the null element based upon the probability of the null element that is predicted.

14. A computer program product according to claim 13 wherein selecting one of the candidate secondary diagnoses comprises selecting the candidate secondary diagnosis having the greatest probability of being contained in the medical chart.

15. A computer program product according to claim 13 wherein predicting the probability of a respective code being contained in the medical chart comprises predicting the probability such that a cumulative probability of the plurality of candidate secondary diagnoses from the set of candidate secondary diagnoses equals 1.

16. A computer program product according to claim 13 wherein determining the categorical crossentropy loss comprises:

for each of the candidate secondary diagnoses that are selected, determining a product of a label representative of a respective candidate secondary diagnosis that is selected and the probability of the respective candidate secondary diagnosis; and summing the products for each of the candidate secondary diagnoses that are selected to determine the categorical crossentropy loss.

17. A computer program product according to claim 13 wherein the operations further comprise adjusting the one or more parameters of the automated coding model based upon the categorical crossentropy loss to reduce the categorical crossentropy loss.

18. A computer program product according to claim 13 wherein removing the candidate secondary diagnosis that has been selected from the set of candidate secondary diagnoses comprises removing the candidate secondary diagnosis that has been selected and one or more additional candidate secondary diagnoses that have a defined relationship to the candidate secondary diagnosis that has been selected from the set of candidate secondary diagnoses.

* * * * *